US011589809B2

(12) United States Patent
Eslami et al.

(10) Patent No.: US 11,589,809 B2
(45) Date of Patent: Feb. 28, 2023

(54) DEVICES, SYSTEMS, AND METHODS FOR LOCATING A POSITION IN A BODY

(71) Applicant: The Board of Regents of the University of Texas System, Austin, TX (US)

(72) Inventors: Vahid Eslami, San Antonio, TX (US); Sahra Emamzadehfard, San Antonio, TX (US); Peter T. Fox, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 455 days.

(21) Appl. No.: 16/866,118

(22) Filed: May 4, 2020

(65) Prior Publication Data

US 2020/0397370 A1 Dec. 24, 2020

Related U.S. Application Data

(60) Provisional application No. 62/842,752, filed on May 3, 2019.

(51) Int. Cl.
*A61B 5/00* (2006.01)
*A61B 90/00* (2016.01)

(52) U.S. Cl.
CPC .......... *A61B 5/4887* (2013.01); *A61B 5/6823* (2013.01); *A61B 5/6831* (2013.01);
(Continued)

(58) Field of Classification Search
CPC ........ A61B 2090/062; A61B 2090/067; A61B 2090/376; A61B 2090/3966;
(Continued)

(56) References Cited

U.S. PATENT DOCUMENTS

| 3,770,956 | A | 11/1973 | Johnson |
| 4,187,423 | A | 2/1980 | Ehrhardt |

(Continued)

FOREIGN PATENT DOCUMENTS

| CA | 2884330 | 3/2014 |
| CN | 106994036 | 8/2017 |

(Continued)

*Primary Examiner* — George Manuel
(74) *Attorney, Agent, or Firm* — Meunier Carlin & Curfman LLC

(57) ABSTRACT

Various implementations include a device for locating a position in a body. The device includes a first body portion. The first body portion has a first longitudinal axis. The device includes a second body portion. The second body portion is slidably coupled to the first body portion. The second body portion has a second longitudinal axis. The device includes a first set of markers disposed on the first body portion for measuring along the first longitudinal axis. The first set of markers includes at least two radiopaque markers. The device also includes a second set of markers disposed on the second body portion for measuring along the second longitudinal axis. The second set of markers includes at least two radiopaque markers. The first body portion is slidable along the second longitudinal axis. The second body portion is slidable along the first longitudinal axis.

20 Claims, 14 Drawing Sheets

(52) U.S. Cl.
CPC .............. A61B 90/06 (2016.02); A61B 90/39 (2016.02); *A61B 2090/062* (2016.02); *A61B 2090/067* (2016.02); *A61B 2090/3966* (2016.02)

(58) Field of Classification Search
CPC ... A61B 5/4887; A61B 5/4896; A61B 5/6823; A61B 5/6831; A61B 90/06; A61B 90/39
See application file for complete search history.

(56) References Cited

U.S. PATENT DOCUMENTS

| | | |
|---|---|---|
| 4,259,585 A | 3/1981 | Novak et al. |
| 4,506,676 A | 3/1985 | Duska |
| 4,813,062 A | 3/1989 | Gilpatrick |
| 4,860,331 A | 8/1989 | Williams et al. |
| 4,985,019 A | 1/1991 | Michelson |
| 5,193,106 A | 3/1993 | Desena |
| 5,232,452 A | 8/1993 | Russell |
| 5,848,125 A | 12/1998 | Arnett |
| 6,972,022 B1 | 12/2005 | Griffin |
| 8,204,575 B2 | 6/2012 | Stetz et al. |
| D742,522 S | 11/2015 | Szabo |
| 9,186,225 B1 | 11/2015 | Pettis |
| D799,696 S | 10/2017 | Sahhr |
| 9,877,846 B2 * | 1/2018 | Dvorak .............. A61B 17/1671 |
| 2004/0127824 A1 | 7/2004 | Falahee |
| 2007/0055290 A1 | 3/2007 | Lober |
| 2008/0009718 A1 | 1/2008 | Zohman |
| 2011/0097134 A1 | 4/2011 | Allen et al. |
| 2012/0302863 A1 | 11/2012 | O'Neill |
| 2015/0272702 A1 | 10/2015 | O'Neill et al. |
| 2016/0324539 A1 | 11/2016 | Sahhar |
| 2017/0156800 A1 | 6/2017 | Brown |
| 2017/0265910 A1 * | 9/2017 | Massengale .............. A61B 6/12 |
| 2019/0021877 A1 | 1/2019 | Federspiel et al. |

FOREIGN PATENT DOCUMENTS

| | | |
|---|---|---|
| CN | 108338825 | 7/2018 |
| JP | 10290797 | 11/1998 |

* cited by examiner

DEVICES, SYSTEMS, AND METHODS FOR LOCATING A POSITION IN A BODY

CROSS-REFERENCE TO RELATED APPLICATIONS

This application claims the benefit of U.S. Provisional Application No. 62/842,752, filed May 3, 2019, the content of which is fully incorporated by reference in its entirety.

BACKGROUND

Physicians and trained registered nurses may be required to perform a lumbar puncture or spinal tap. A physician or trained registered nurse often needs to puncture the lumbar between vertebra to successfully perform a spinal tap. In most cases, the physician or trained registered nurse will perform a bedside lumbar puncture wherein the physician or trained registered nurse noninvasively determines the location of a lumbar puncture. As an alternative, the performing physician or trained registered nurse may attempt a lumbar puncture using ultrasound guidance, but ultrasound guided lumbar puncture is not easy, very tech dependent, and almost unhelpful in obese patients due to the patient's fat mass. Also, performing a lumbar puncture while having the ultrasound in one hand in a sterile environment and a lumbar puncture needle in another hand can prove difficult. A physician or trained registered nurse may only make these additional attempts if comfortable and familiar with ultrasound. The physician or trained registered nurse may otherwise consult a radiology group for a fluoroscopy-guided lumbar puncture, which may be susceptible to spatial blurring and temporal blurring. While physicians in internal medicine, emergency medicine, and neurology have historically performed lumbar punctures, radiologists are now the dominant provider of this procedure in difficult and obese cases. Many clinical facilities, particularly small hospitals or clinics in rural or underserved communities, are not equipped with radiologists on-site to perform this procedure. However, access to portable X-ray is common.

Furthermore, fluoroscopy-guided lumbar puncture can result in excessive exposure of radiation to the patient. Thus, there exists a need for a less-invasive device and method to determine the location of a spinal tap using X-ray.

SUMMARY

Various implementations include a device for locating a position in a body. The device includes a first body portion. The first body portion has a first longitudinal axis. The device includes a second body portion. The second body portion is slidably coupled to the first body portion. The second body portion has a second longitudinal axis. The device includes a first set of markers disposed on the first body portion for measuring along the first longitudinal axis. The first set of markers includes at least two radiopaque markers. The device also includes a second set of markers disposed on the second body portion for measuring along the second longitudinal axis. The second set of markers includes at least two radiopaque markers. The first body portion is slidable along the second longitudinal axis. The second body portion is slidable along the first longitudinal axis.

In some implementations, the longitudinal axis is disposed perpendicular to the second longitudinal axis.

In some implementations, the first set of markers measure distance along the first longitudinal axis.

In some implementations, the second set of markers measure distance along the second longitudinal axis.

In some implementations, the first body portion and the second body portion are radio-translucent.

In some implementations, the device includes an adhesive material disposed on a surface of the first body portion, the second body portion, or both.

In some implementations, the first body portion and the second body portion are made of an acrylic material.

In some implementations, the device includes a protractor body portion coupled to the first body portion and the second body portion. The device includes a set of protractor markers disposed on the protractor body portion for measuring an angle relative to the first longitudinal axis. The set of protractor markers can include at least two radiopaque markers.

In some implementations, the protractor body portion is slidable along the first longitudinal axis.

In some implementations, the protractor body portion is radio-translucent.

Various other implementations include an angle of insertion device. The device includes a first body portion having a longitudinal axis and a protractor body portion coupled to the first body portion. The device includes a first set of markers disposed on the first body portion for measuring along the longitudinal axis. The first set of markers includes at least two radiopaque markers. The device includes a set of protractor markers disposed on the protractor body portion for measuring an angle relative to the longitudinal axis. The set of protractor markers includes at least two radiopaque markers.

In some implementations, the protractor body portion is slidable along the first longitudinal axis.

In some implementations, the first set of markers measure distance along the first longitudinal axis.

In some implementations, the first body portion and the protractor body portion are radio-translucent.

In some implementations, the device includes an adhesive material disposed on a surface of the first body portion, the protractor body portion, or both.

In some implementations, the first body portion and the protractor body portion are made of an acrylic material.

In some implementations, the longitudinal axis is a first longitudinal axis. The device also includes a second body portion slidably coupled to the first body portion, the second body portion having a second longitudinal axis. The device includes a second set of markers disposed on the second body portion for measuring along the second longitudinal axis. The second set of markers includes least two radiopaque markers.

In some implementations, the first body portion is slidable along the second longitudinal axis, and the second body portion is slidable along the first longitudinal axis.

Various implementations include a system for locating a position in a body. The system includes a device for locating a position in a body, an angle of insertion device, and a belt for being disposed around a waist and/or hips of a person. The belt includes a dorsal belt portion and a side belt portion. The dorsal belt portion is for being disposed adjacent a sagittal plane on a dorsal side of the person. The dorsal belt portion includes a first coupler for coupling the device for locating a position in a body to the belt. The side belt portion is for being disposed adjacent a coronal plane of the person. The side belt portion includes a second coupler for coupling the angle of insertion device to the belt.

In some implementations, the first coupler is slidable relative to the belt along a belt longitudinal axis. In some implementations, the second coupler is slidable relative to the belt along a belt longitudinal axis.

In some implementations, the device for locating a position in a body is slidably couplable to the first coupler of the dorsal belt portion. In some implementations, the angle of insertion device is slidably couplable to the second coupler of the side belt portion.

In some implementations, the belt defines one or more calibration holes for determining whether the belt has moved relative to a patient. The one or more calibration holes extend from an outer surface of the belt to an inner surface of the belt.

Various other implementations include a method of determining the location of an intervertebral space. The method includes providing a device for locating a position in a body. The device includes a first body portion having a first longitudinal axis. The device includes a second body portion slidably coupled to the first body portion. The second body portion has a second longitudinal axis. The device includes a first set of markers disposed on the first body portion for measuring along the first longitudinal axis. The first set of markers includes at least two radiopaque markers. The device includes a second set of markers disposed on the second body portion for measuring along the second longitudinal axis. The second set of markers includes at least two radiopaque markers. In some implementations the first body portion is slidable along the second longitudinal axis, and the second body portion is slidable along the first longitudinal axis. The method includes disposing the device for locating a position in a body on the back of a subject. The method includes producing a first X-ray image of the subject and the device for locating a position in a body. In some implementations, the first X-ray image is taken perpendicular to a plane defined by the first longitudinal axis and the second longitudinal axis. The method includes determining a vertical location of an intervertebral space based on a position of the first set of markers and the second set of markers in the first X-ray image.

In some implementations, the device for locating a position in a body further comprises an adhesive material disposed on a surface of the first body portion, the second body portion, or both.

In some implementations, the first body portion and the second body portion are made of an acrylic material.

In some implementations, the first longitudinal axis is disposed perpendicular to the second longitudinal axis.

In some implementations, the first set of markers measure distance along the first longitudinal axis.

In some implementations, the second set of markers measure distance along the second longitudinal axis.

In some implementations, the first body portion and the second body portion are radio-translucent.

In some implementations, the device for locating a position in a body further includes a protractor body portion coupled to the first body portion and the second body portion. The device includes a set of protractor markers disposed on the protractor body portion for measuring an angle relative to the first longitudinal axis. The set of protractor markers includes at least two radiopaque markers.

In some implementations, the protractor body portion is slidable along the first longitudinal axis.

In some implementations, the protractor body portion is radio-translucent.

In some implementations, the method includes providing an angle of insertion device. The device includes a first body portion having a longitudinal axis. The device includes a protractor body portion coupled to the first body portion. The device includes a first set of markers disposed on the first body portion for measuring along the longitudinal axis. The first set of markers includes at least two radiopaque markers. The device includes a set of protractor markers disposed on the protractor body portion for measuring an angle relative to the longitudinal axis. The set of protractor markers includes at least two radiopaque markers. The method includes disposing the angle of insertion device on the side of the subject. In some implementations the longitudinal axis of the angle of insertion device is perpendicular to the back plane, and the longitudinal axis of the angle of insertion device and the vertical location of the intervertebral space are intersected by an axis perpendicular to a sagittal plane of the subject. The method includes producing a second X-ray image of the subject and the angle of insertion device, wherein the second X-ray image is taken perpendicular to the sagittal plane of the subject. The method includes determining an angle of insertion for an instrument into the intervertebral space based on a position of the set of protractor markers of the angle of insertion device in the second X-ray image.

In some implementations the method includes determining a depth of insertion for an instrument into the intervertebral space based on a position of the first set of markers of the angle of insertion device in the second X-ray image.

In some implementations the method includes determining a point of entry on the back of the subject based on the vertical location of the intervertebral space, the angle of insertion, and the depth of insertion.

In some implementations, the protractor body portion is slidable along the first longitudinal axis of the angle of insertion device.

In some implementations, the first set of markers measure distance along the first longitudinal axis of the angle of insertion device.

In some implementations, the first body portion and the protractor body portion of the angle of insertion device are radio-translucent.

In some implementations, the longitudinal axis of the angle of insertion device is a first longitudinal axis. The device includes a second body portion slidably coupled to the first body portion of the angle of insertion device, the second body portion having a second longitudinal axis. The device includes a second set of markers disposed on the second body portion of the angle of insertion device for measuring along the second longitudinal axis of the angle of insertion device. The second set of markers includes at least two radiopaque markers.

In some implementations the first body portion of the angle of insertion device is slidable along the second longitudinal axis of the angle of insertion device. In some implementations the second body portion of the angle of insertion device is slidable along the first longitudinal axis of the lumbar puncture angle device.

In some implementations, the method includes disposing the device for locating a position in a body on the side of the subject. The first longitudinal axis is perpendicular to the back plane, and the first longitudinal axis and the vertical location of the intervertebral space are intersected by an axis perpendicular to a sagittal plane of the subject. The method includes producing a second X-ray image of the subject and the device for locating a position in a body. In some implementations, the second X-ray image is taken perpendicular to the sagittal plane of the subject. The method includes determining an angle of insertion for an instrument into the intervertebral space based on a position of the set of protractor markers in the second X-ray image.

In some implementations the method includes determining a depth of insertion for an instrument into the intervertebral space based on a position of the first set of markers in the second X-ray image.

In some implementations, the method includes determining a point of entry on the back of the subject based on the vertical location of the intervertebral space, the angle of insertion, and the depth of insertion.

In some implementations, the protractor body portion is slidable along the first longitudinal axis.

In some implementations, the protractor body portion is radio-translucent.

In some implementations, the subject is lying in a lateral decubitus position.

DETAILED DESCRIPTION

Figure 1:
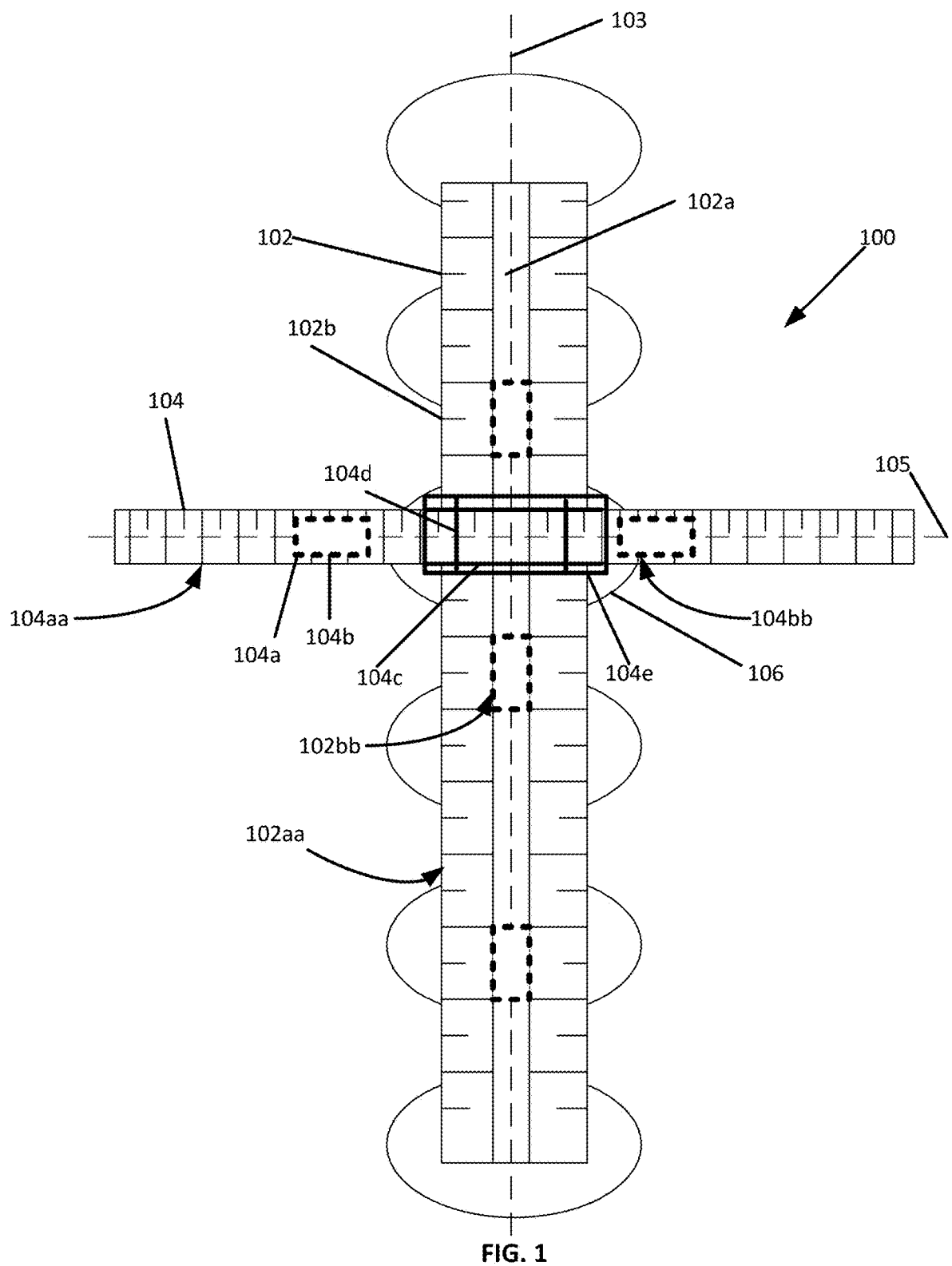
FIG. 1 is a top view of a bone device for locating a position in a body, according to one implementation.

Various implementations include a device for locating a position in a body. The device includes a first body portion. The first body portion has a first longitudinal axis. The device includes a second body portion. The second body portion is slidably coupled to the first body portion. The second body portion has a second longitudinal axis. The device includes a first set of markers disposed on the first body portion for measuring along the first longitudinal axis. The first set of markers includes at least two radiopaque markers. The device also includes a second set of markers disposed on the second body portion for measuring along the second longitudinal axis. The second set of markers includes at least two radiopaque markers. The first body portion is slidable along the second longitudinal axis. The second body portion is slidable along the first longitudinal axis.

Various other implementations include an angle of insertion device. The device includes a first body portion having a longitudinal axis and a protractor body portion coupled to the first body portion. The device includes a first set of markers disposed on the first body portion for measuring along the longitudinal axis. The first set of markers includes at least two radiopaque markers. The device includes a set of protractor markers disposed on the protractor body portion for measuring an angle relative to the longitudinal axis. The set of protractor markers includes at least two radiopaque markers.

Various other implementations include a system for locating a position in a body. The system includes a device for locating a position in a body, an angle of insertion device, and a belt for being disposed around a waist and/or hips of a person. The belt includes a dorsal belt portion and a side belt portion. The dorsal belt portion is for being disposed adjacent a sagittal plane on a dorsal side of the person. The dorsal belt portion includes a first coupler for coupling the device for locating a position in a body to the belt. The side belt portion is for being disposed adjacent a coronal plane of the person. The side belt portion includes a second coupler for coupling the angle of insertion device to the belt.

Various other implementations include a method of determining the location of an intervertebral space. The method includes providing a device for locating a position in a body. The device includes a first body portion having a first longitudinal axis. The device includes a second body portion slidably coupled to the first body portion. The second body portion has a second longitudinal axis. The device includes a first set of markers disposed on the first body portion for measuring along the first longitudinal axis. The first set of markers includes at least two radiopaque markers. The device includes a second set of markers disposed on the second body portion for measuring along the second longitudinal axis. The second set of markers includes at least two radiopaque markers. In some implementations the first body portion is slidable along the second longitudinal axis, and the second body portion is slidable along the first longitudinal axis. The method includes disposing the device for locating a position in a body on the back of a subject. The method includes producing a first X-ray image of the subject and the device for locating a position in a body. In some implementations, the first X-ray image is taken perpendicular to a plane defined by the first longitudinal axis and the second longitudinal axis. The method includes determining a vertical location of an intervertebral space based on a position of the first set of markers and the second set of markers in the first X-ray image.

FIG. 1 shows a device for locating a position in a body 100. The device for locating a position in a body 100 includes a first body portion 102 and a second body portion 104. The first body portion 102 has a contact surface 102*aa*, an outside surface 102*a* spaced apart and opposite the contact surface 102aa, and a longitudinal axis 103. The first body portion 102 has a set of markers 102b disposed on the outside surface 102a. The set of markers 102b is disposed in increments along the longitudinal axis 103 of the first body portion 102. The set of markers 102b is manufactured from a radiopaque material. For example, the set of markers 102b can be made of barium sulfate, bismuth compounds, tungsten metals, a blend of these materials, or any material with a high mass attenuation coefficient that makes the material clearly visible under X-rays without sacrificing the mechanical properties of the material. The first body portion 102 is manufactured from Acrylic, but in other implementations, the first body portion is manufactured from ABS plastic, polycarbonate, or any firm but radiolucent material with a low mass attenuation coefficient. Thus, when the device 100 is viewed in an X-ray image, the set of markers 102b is visible, but the first body portion 102 is not visible. An adhesive material 102bb is disposed on the contact surface 102aa such that the first body portion 102 is couplable to a patient via the adhesive material 102bb. Although the adhesive material 102bb shown in FIG. 1 is a double-sided tape, in some implementations, the adhesive material is a glue, suction device, or any other adhesive material capable of coupling the device to a patient while locating the desired entry point. Although the set of markers 102b shown in FIG. 1 are disposed on the outside surface 102a, in some implementations, the set of markers can be disposed on the contact surface or embedded within the first body portion.

The second body portion 104 has a contact surface 104aa, an outside surface 104a spaced apart and opposite from the contact surface 104aa, and a longitudinal axis 105. The second body portion 104 has a set of markers 104b disposed on the outside surface 104a. The set of markers 104b are disposed in increments along the longitudinal axis 105 of the second body portion 104. The set of markers 104b is made of a radiopaque material. For example, the set of markers 104b can be made of barium sulfate, bismuth compounds, tungsten metals, a blend of these materials, or any material with a high mass attenuation coefficient that makes the material clearly visible under X-rays without sacrificing the mechanical properties of the material. The second body portion 104 is manufactured from acrylic, but in other implementations, the first body portion is manufactured from ABS plastic, polycarbonate, or any firm but radiolucent material with a low mass attenuation coefficient. Thus, when the device 100 is viewed in an X-ray image, the set of markers 104b is visible, but the first body portion 104 is not visible. An adhesive material 104bb is disposed on the contact surface 104aa such that the first body portion 104 is couplable to a patient via the adhesive material 104bb. Although the adhesive material 104bb shown in FIG. 1 is a double-sided tape, in some implementations, the adhesive material is a glue, suction device, or any other adhesive material capable of coupling the device to a patient while locating the desired entry point. Although the set of markers 104b shown in FIG. 1 are disposed on the outside surface 104a, in some implementations, the set of markers can be disposed on the contact surface or embedded within the first body portion.

The first body portion 102 and the second body portion 104 are connected such that the contact surface 104aa of the second body portion 104 and the contact surface 102aa of the first body portion 102 are parallel to each other. The longitudinal axis 103 of the first body portion 102 is perpendicular to the longitudinal axis 105 of the second body portion 104. The first body portion 102 is coupled to the second body portion 104 with a sliding mechanism 104c.

The sliding mechanism 104c has two grooves 104d that are parallel with the longitudinal axis 103 of the first body portion 102 and two grooves 104e that are parallel with the longitudinal axis 105 of the second body portion 104. Portions of the first body portion 102 are disposed within the two grooves 104d and portions of the second body portion 104 are disposed within the two grooves 104e. Although the first body portion 102 and the second body portion 104 are coupled to each other using the sliding mechanism in FIG. 1, in some implementations the first body portion and the second body portion are coupled using a ball and track joint, a protrusion slidably disposed in a slot, or any other means capable of slidably coupling first body portion to the second body portion. The second body portion 104 is configured and connected such that it can slide across the first body portion 102 in a direction parallel to the longitudinal axis 103 of the first body portion 102 and the first body portion 102 can slide across the second body portion 104 in a direction parallel to the longitudinal axis 105 of the second body portion 104. However, the sliding mechanism 104c firmly couples the first body portion 102 and the second body portion 104 such that the first body portion 102 and the second body portion 104 do not slide without force exerted on them. The longitudinal axis 105 of the second body portion 104 is perpendicular to the longitudinal axis 103 of the first body portion 102. According to some implementations, the first body portion 102 and the second body portion 104 are restricted from rotating with respect to each other.

Although the device for locating a position in a body 100 shown in FIG. 1 includes a first body portion 102 and a second body portion 104, in some implementations, the device for locating a position in a body includes only one grid portion that includes a first longitudinal axis, a second longitudinal axis perpendicular to the first longitudinal axis, and sets of radiopaque markers disposed along the first and second longitudinal axes.

Figure 2:
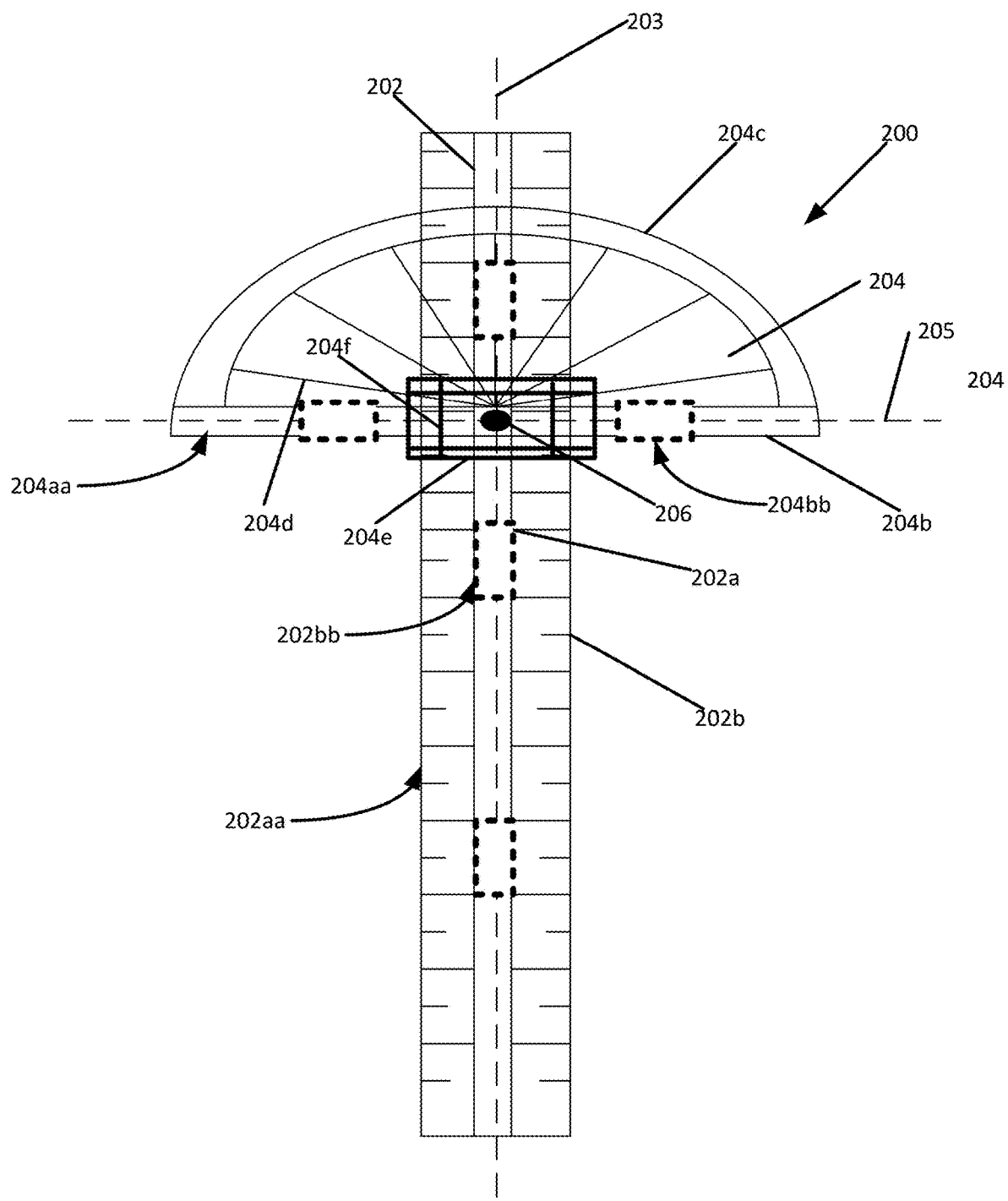
FIG. 2 is a side view of an implementation of the angle of insertion device.

FIG. 2 shows an angle of insertion device 200. The angle of insertion device 200 includes a first body portion 202 and a protractor body 204. The first body portion 202 has a contact surface 202aa, an outside surface 202a spaced apart and opposite the contact surface 202aa, and a longitudinal axis 203. The first body portion 202 has a set of markers 202b disposed on the outside surface 202a. The set of markers 202b is disposed in increments along the longitudinal axis 203 of the first body portion 202. The set of markers 202b is manufactured from a radiopaque material. For example, the set of markers 202b can be made of barium sulfate, bismuth compounds, tungsten metals, a blend of these materials, or any material with a high mass attenuation coefficient that makes the material clearly visible under X-rays without sacrificing the mechanical properties of the material. The first body portion 202 is manufactured from acrylic, but in other implementations, the first body portion is manufactured from ABS plastic, polycarbonate, or any firm but radiolucent material with a low mass attenuation coefficient. Thus, when the device 200 is viewed in an X-ray image, the set of markers 202b is visible, but the first body portion 202 is not visible. An adhesive material 202bb is disposed on the contact surface 202aa such that the first body portion 202 is couplable to a patient via the adhesive material 202bb. Although the adhesive material 202bb shown in FIG. 2 is a double-sided tape, in some implementations, the adhesive material is a glue, suction device, or any other adhesive material capable of coupling the device to a patient while locating the desired entry point. Although the set of markers 202b shown in FIG. 2 are disposed on the outside surface 202a, in some implementations, the set of markers can be disposed on the contact surface or embedded within the first body portion.

The protractor body 204 has a contact surface 204aa and an outside surface 204a spaced apart and opposite the contact surface 204aa. The protractor body 204 includes a horizontal bar 204b, having a longitudinal axis 205, and a semicircle body 204c. The semicircle body 204b has a center that is equidistant between two ends of the semicircle body 204c. The two ends of the semicircle body 204c are aligned with two ends of the horizontal bar 204b, and the center point are configured such that a straight line bisecting the center of the semicircle body 204c can also bisect the center point of the horizontal bar 204b and is perpendicular to the horizontal bar 204b longitudinal axis 205. The protractor body 204 is manufactured from acrylic, but in other implementations, the first body portion is manufactured from ABS plastic, polycarbonate, or any firm but radiolucent material with a low mass attenuation coefficient.

According to some implementations, the protractor body 204 can rotate around a rotation point 206 on the first body portion 202. The protractor body 204 can also slide along the longitudinal axis 203 on the first body portion 202. The protractor body 204 can also be connected to the first body portion 202, such that a user can rotate the protractor body 204 independently of the first body portion 202. The protractor body 204 is coupled to the first body portion 202 with a sliding mechanism 204e.

The sliding mechanism 204e has two grooves 204f that are parallel with the longitudinal axis 203 of the first body portion 202. Portions of the first body 202 are disposed within the two grooves 204f. Although the first body portion 202, and the protractor body portion 204 are coupled to each other using the sliding mechanism in FIG. 2, in some implementations the first body portion and the protractor body portion are coupled using a ball and track joint, a protrusion slidably disposed in a slot, or any other means capable of slidably coupling first body portion 202 relative to the protractor body portion 204. The protractor body portion 204 is configured and connected such that it can slide across the first body portion 202 in a direction parallel to the longitudinal axis 203 of the first body portion 202. However, the sliding mechanism 204e firmly couples the first body portion 202 and the protractor body portion 204 such that the first body portion 202 and the protractor body portion 204 do not slide without force exerted on them.

The protractor body 204 has a set of markers 204d. The set of markers 204d in FIG. 2 are disposed on the outside surface 204a of the first protractor body 204, but in other implementations, the set of markers are embedded in the first protractor body or are disposed on the contact surface. The set of markers 204d can be made of barium sulfate, bismuth compounds, tungsten metals, a blend of these materials, or any material with a high mass attenuation coefficient that makes the material clearly visible under X-rays without sacrificing the mechanical properties of the material.

In use, the device for locating a position in a body 100 can be used for locating a position in a body 100 to determine the correct location for lumbar puncture. The second body portion 104, is configured such that it can be situated adjacent to a spinal column 106. As discussed above, the first body portion 102 and the second body portion 104 are configured such that they are not visible through an X-ray scan, while the markers 102b, 104b are visible to an X-ray scan. The adhesive material 102bb, 104bb is disposed on the contact surfaces 102aa, 104aa such that the first body portion 102 and second body portions 104 are coupled to a patient via the adhesive material 102bb. The user can view the spinal column of the patient in an X-ray image relative to the radiopaque sets of markers 102b, 104b to determine the location of an intervertebral gap.

The user can use the angle of insertion device 200 to then determine the angle and depth of inserting of a needle. The protractor body 204 can be configured along the side of a patient such that the horizontal bar 202b is horizontally aligned with a patient's back and the first body portion 202 longitudinal axis 203 aligns with the location of the intervertebral gap determined in using the device for locating a position in a body 100. The user can view the spinal column of the patient in a second X-ray image relative to the radiopaque set of markers 202b of the first body portion 202 to determine the depth of the intervertebral gap relative to the skin of the patient's back. The user can also use the radiopaque sets of markers 204d of the protractor body portion 204 to determine the correct angle of insertion of the intervertebral gap. As such, a user such as a physician can use the invention to act as a guide for a lumbar puncture.

Figure 3:
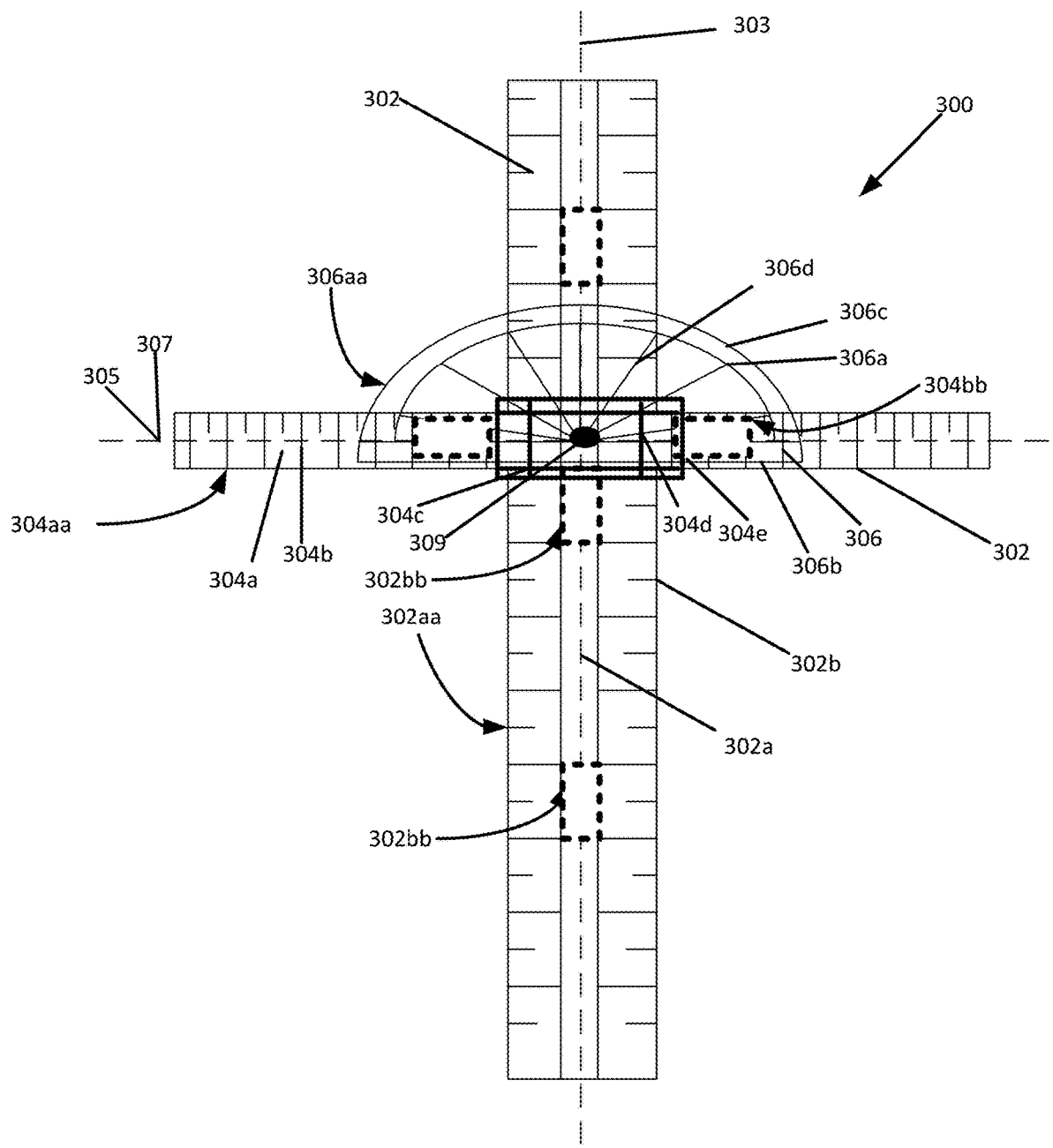
FIG. 3 is a side view of an implementation of the angle of insertion device.

FIG. 3 shows an angle of insertion device 300. The angle of insertion device 300 includes a first body portion 302, a second body portion 304, and a protractor body 306. The first body portion 302 has a contact surface 302aa, an outside surface 302a spaced apart and opposite the contact surface 302aa, and a longitudinal axis 303. The first body portion 302 has a set of markers 302b disposed on the outside surface 302a. The set of markers 302b are disposed in increments along the longitudinal axis 303 of the first body portion 302. The set of markers 302b is manufactured from a radiopaque material. For example, the set of markers 302a can be made of barium sulfate, bismuth compounds, tungsten metals, a blend of these materials, or any material with a high mass attenuation coefficient that makes the material clearly visible under X-rays without sacrificing the mechanical properties of the material. The first body portion 302 is manufactured from acrylic, but in other implementations, the first body portion is manufactured from ABS plastic, polycarbonate, or any firm but radiolucent material with a low mass attenuation coefficient. Thus, when the device 300 is viewed in an X-ray image, the set of markers 302b is visible, but the first body portion 302 is not visible. An adhesive material 302bb is disposed on the contact surface 302aa such that the first body portion 302 is couplable to a patient via the adhesive material 302bb. Although the adhesive material 302bb shown in FIG. 3 is a double-sided tape, in some implementations, the adhesive material is a glue, suction device, or any other adhesive material capable of coupling the device to a patient while locating the desired entry point. Although the set of markers 302b shown in FIG. 3 is disposed on the outside surface 302a, in some implementations, the set of markers can be disposed on the contact surface or embedded within the first body portion.

The second body portion 304 has a contact surface 304aa, an outside surface 304a spaced apart and opposite from the contact surface 304aa, and a longitudinal axis 305. The second body portion 304 has a set of markers 304b disposed on the outside surface 304a. The set of markers 304b is disposed in increments along the longitudinal axis 305 of the second body portion 304. The set of markers 304b is made of a radiopaque material. For example, the set of markers 304b can be made of barium sulfate, bismuth compounds, tungsten metals, a blend of these materials, or any material with a high mass attenuation coefficient that makes the material clearly visible under X-rays without sacrificing the mechanical properties of the material. The second body portion 304 is manufactured from acrylic, but in other implementations, the first body portion is manufactured from ABS plastic, polycarbonate, or any firm but radiolucent material with a low mass attenuation coefficient. Thus, when the device 300 is viewed in an X-ray image, the set of markers 304b is visible, but the second body portion 304 is not visible. An adhesive material 304bb is disposed on the contact surface 304aa such that the second body portion 304 is couplable to a patient via the adhesive material 304bb. Although the adhesive material 304bb shown in FIG. 3 is a double-sided tape, in some implementations, the adhesive material is a glue, suction device, or any other adhesive material capable of coupling the device to a patient while locating the desired entry point. Although the set of markers 304b shown in FIG. 3 are disposed on the outside surface 304a, in some implementations, the set of markers can be disposed on the contact surface or embedded within the first body portion.

The first body portion 302 and the second body portion 304 are connected such that the contact surface 304aa of the second body portion 304 and the contact surface 302aa of the first body portion 302 are parallel to each other. The longitudinal axis 303 of the first body portion 302 is perpendicular to the longitudinal axis 305 of the second body portion 304. The first body portion 302 is coupled to the second body portion 304 with a sliding mechanism 304c. The sliding mechanism 304c has two grooves 304d that are parallel with the longitudinal axis 303 of the first body portion 302 and two grooves 304e that are parallel with the longitudinal axis 305 of the second body portion 304. Portions of the first body portion 302 are disposed within the two grooves 304d and portions of the second body portion 304 are disposed within the two grooves 304e. Although the first body portion 302 and the second body portion 304 are coupled to each other using the sliding mechanism in FIG. 3, in some implementations the first body portion and the second body portion are coupled using a ball and track joint, a protrusion slidably disposed in a slot, or any other means capable of slidably coupling first body portion to the second body portion. The second body portion 304 is configured and connected such that it can slide across the first body portion 302 in a direction parallel to the longitudinal axis 303 of the first body portion 302 and the first body portion 302 can slide across the second body portion 304 in a direction parallel to the longitudinal axis 305 of the second body portion 304. However, the sliding mechanism 304c firmly couples the first body portion 302 and the second body portion 304 such that the first body portion 302 and the second body portion 304 do not slide without force exerted on them. The longitudinal axis 305 of the second body portion 304 is perpendicular to the longitudinal axis 303 of the first body portion 302. According to some implementations, the first body portion 302 and the second body portion 304 are restricted from rotating with respect to each other.

The protractor body 306 has a contact surface 306aa and an outside surface 306a spaced apart and opposite the contact surface 306aa. The protractor body 306 includes a horizontal bar 306b, having a longitudinal axis 305, and a semicircle body 306c. The semicircle body 306c has a center that is equidistant between two ends of the semicircle body 306c. The two ends of the semicircle body 306c are aligned with two ends of the horizontal bar 306b, and the center point is configured such that a straight line bisecting the center of the semicircle body 306c can also bisect the center point of the horizontal bar 306b and is perpendicular to the horizontal bar 306b longitudinal axis 305. The protractor body 306 is manufactured from acrylic, but in other implementations, the first body portion is manufactured from ABS plastic, polycarbonate, or any firm but radiolucent material with a low mass attenuation coefficient According to some implementations, the protractor body 306 can rotate around a rotation point 306 on the first body portion 302. The protractor body 306 can also slide along the longitudinal axis 303 on the first body portion 302. The protractor body 306 can also be connected to the first body portion 302, such that a user can rotate the protractor body 306 independently of the first body portion 302. The protractor body 306 is coupled to the first body portion 302 with a sliding mechanism 304e.

The sliding mechanism 304c has two grooves 304d that are parallel with the longitudinal axis 303 of the first body portion 302. Portions of the first body 302 are disposed within the two grooves 304d. Although the first body portion 302, and the protractor body portion 306 are coupled to each other using the sliding mechanism in FIG. 3, in some implementations the first body portion and the protractor body portion are coupled using a ball and track joint, a protrusion slidably disposed in a slot, or any other means capable of slidably coupling first body portion 302 relative to the protractor body portion 304. The protractor body portion 306 is configured and connected such that it can slide across the first body portion 302 in a direction parallel to the longitudinal axis 303 of the first body portion 302. However, the sliding mechanism 304c firmly couples the first body portion 302 and the protractor body portion 306 such that the first body portion 302 and the protractor body portion 306 do not slide without force exerted on them.

The protractor body 306 has a set of markers 306d. The set of markers 306d in FIG. 3 are disposed on the outside surface 306a of the first protractor body 306, but in other implementations, the set of markers are embedded in the first protractor body or are disposed on the contact surface. The set of markers 306d can be made of barium sulfate, bismuth compounds, tungsten metals, a blend of these materials, or any material with a high mass attenuation coefficient that makes the material clearly visible under X-rays without sacrificing the mechanical properties of the material In use, the device for locating a position in a body 300 can be used for locating a position in a body 300 to determine the correct location for lumbar puncture. The second body portion 304, is configured such that it can be situated adjacent to a spinal column. As discussed above, the first body portion 302, the second body portion, and the protractor body 306 are configured such that they are not visible through an X-ray scan, while the markers 302b, 304b, 306d are visible to an X-ray scan. The adhesive material 302bb, 304bb is disposed on the contact surfaces 302aa, 304aa such that the first body portion 302 and second body portions 304 are coupled to a patient via the adhesive material 302bb. The user can view the spinal column of the patient in an X-ray image relative to the radiopaque sets of markers 302b, 304b to determine the location of an intervertebral gap.

The user can use the angle of insertion device 300 to then determine the angle and depth of inserting of a needle. The protractor body 306 can be configured along the side of a patient such that the horizontal bar 306b is horizontally aligned with a patient's back and the first body portion 302 longitudinal axis 303 aligns with the location of the intervertebral gap determined in using the angle of insertion device 300. The user can view the spinal column of the patient in a second X-ray image relative to the radiopaque set of markers 302b of the first body portion 302 to determine the depth of the intervertebral gap relative to the patient's back. The user can also use the radiopaque sets of markers 306d of the protractor body portion 306 to determine the correct angle of insertion to the space of the intervertebral gap. As such, a user such as a physician can use the invention to act as a guide for a lumbar puncture.

Figure 4A:
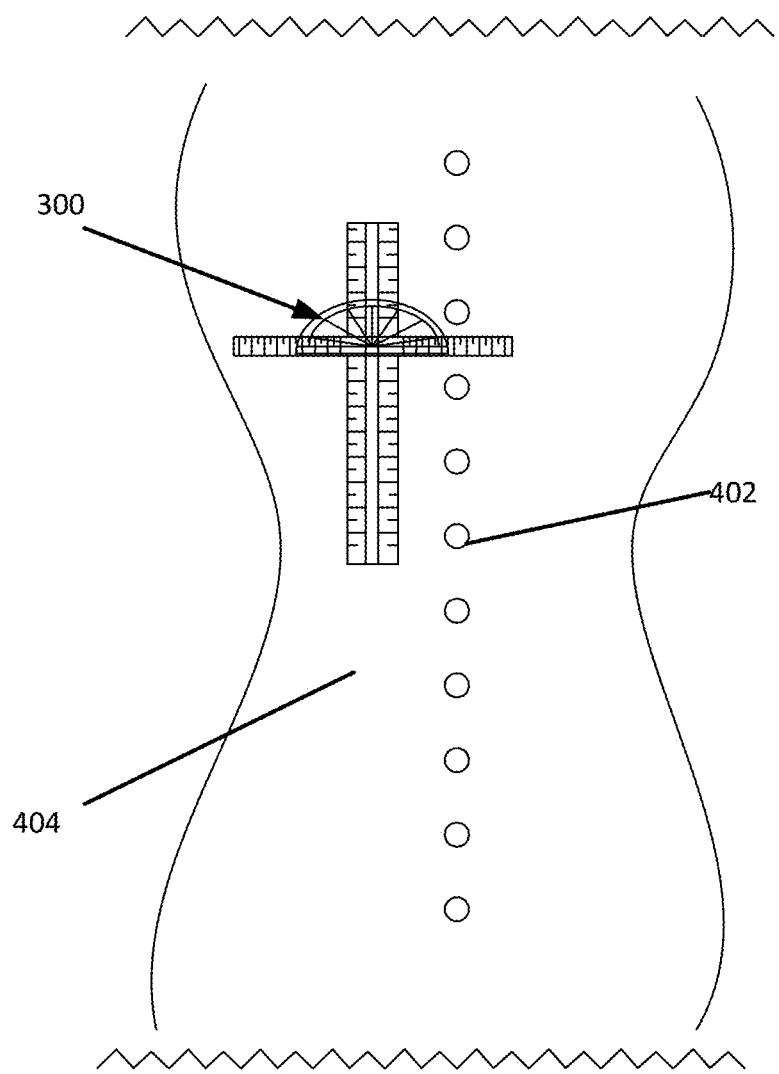
FIG. 4A is a top view of the angle of insertion device of FIG. 3 in alignment with a vertebra and configured to measure a lumbar puncture location.
Figure 4B:
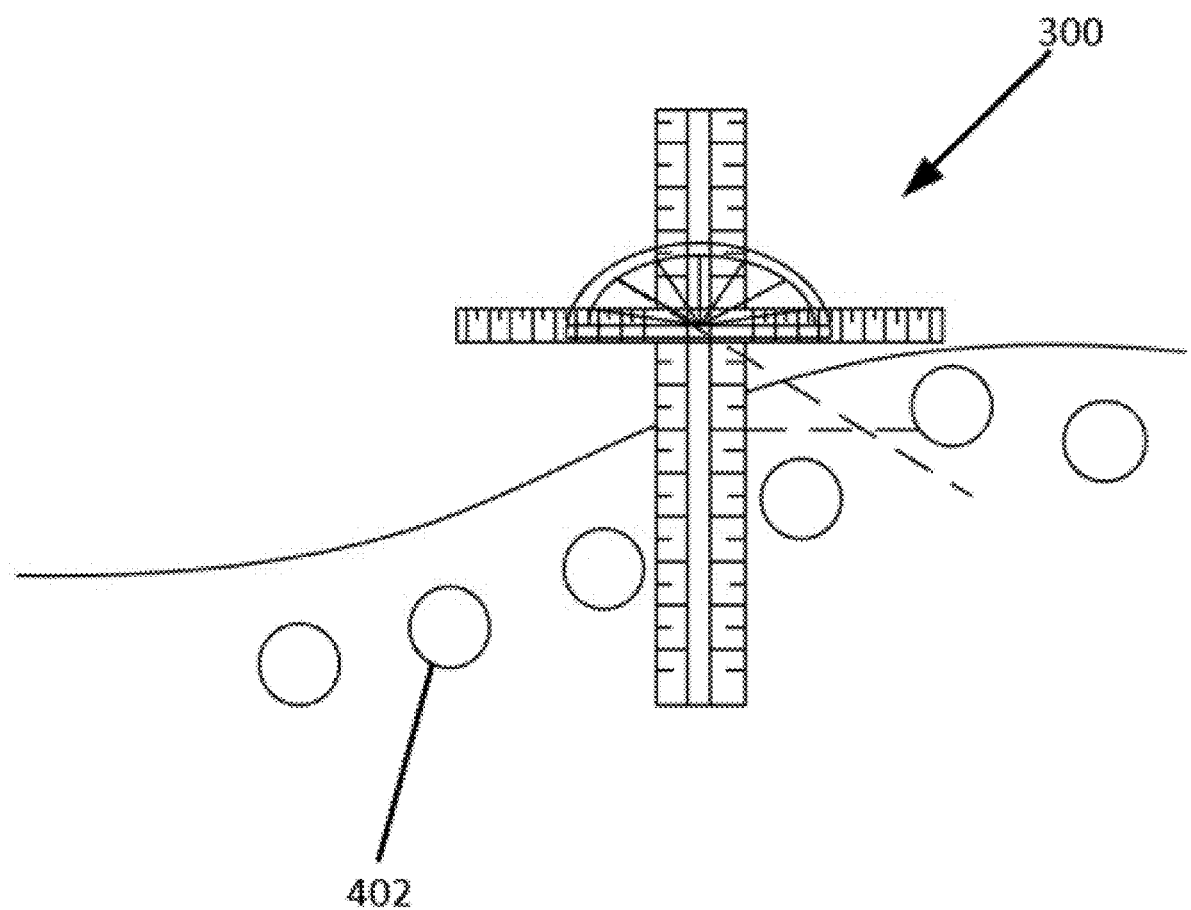
FIG. 4B is a side view of the angle of insertion device of FIG. 3 in alignment with a vertebra and configured to measure a lumbar puncture location, angle, and depth of insertion, showing line traces to determine insertion point.
Figure 4C:
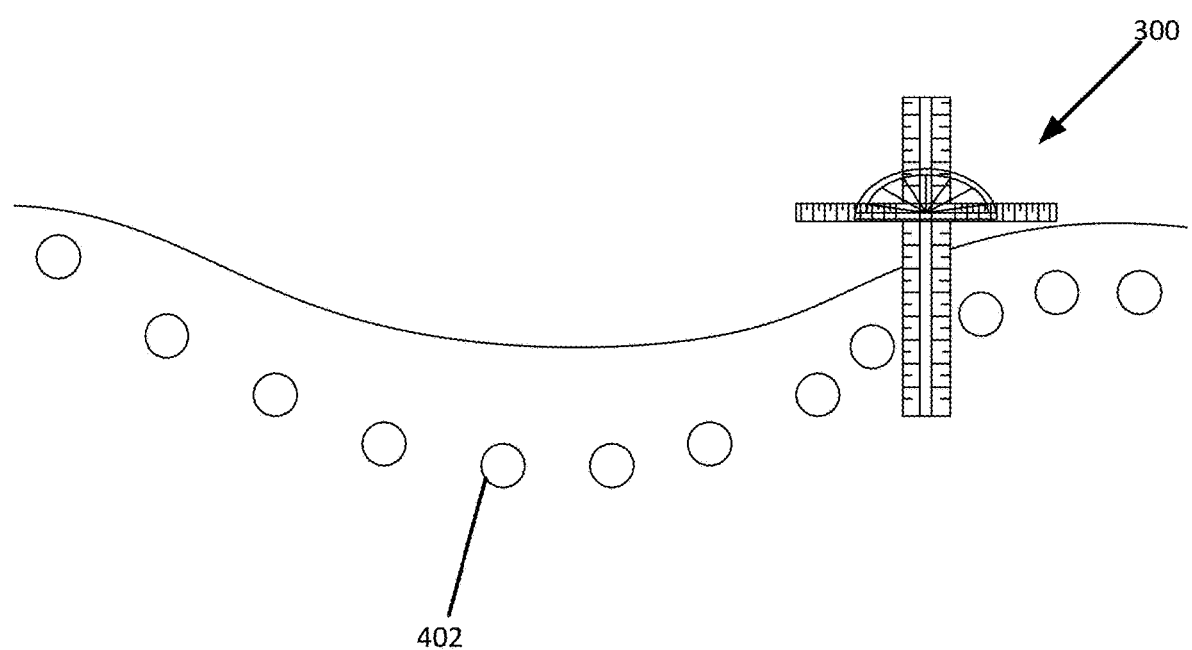
FIG. 4C is a side view of an of the angle of insertion device of FIG. 3 in alignment with a vertebra and configured to measure a lumbar puncture location, angle, and depth of insertion.
Figure 5:
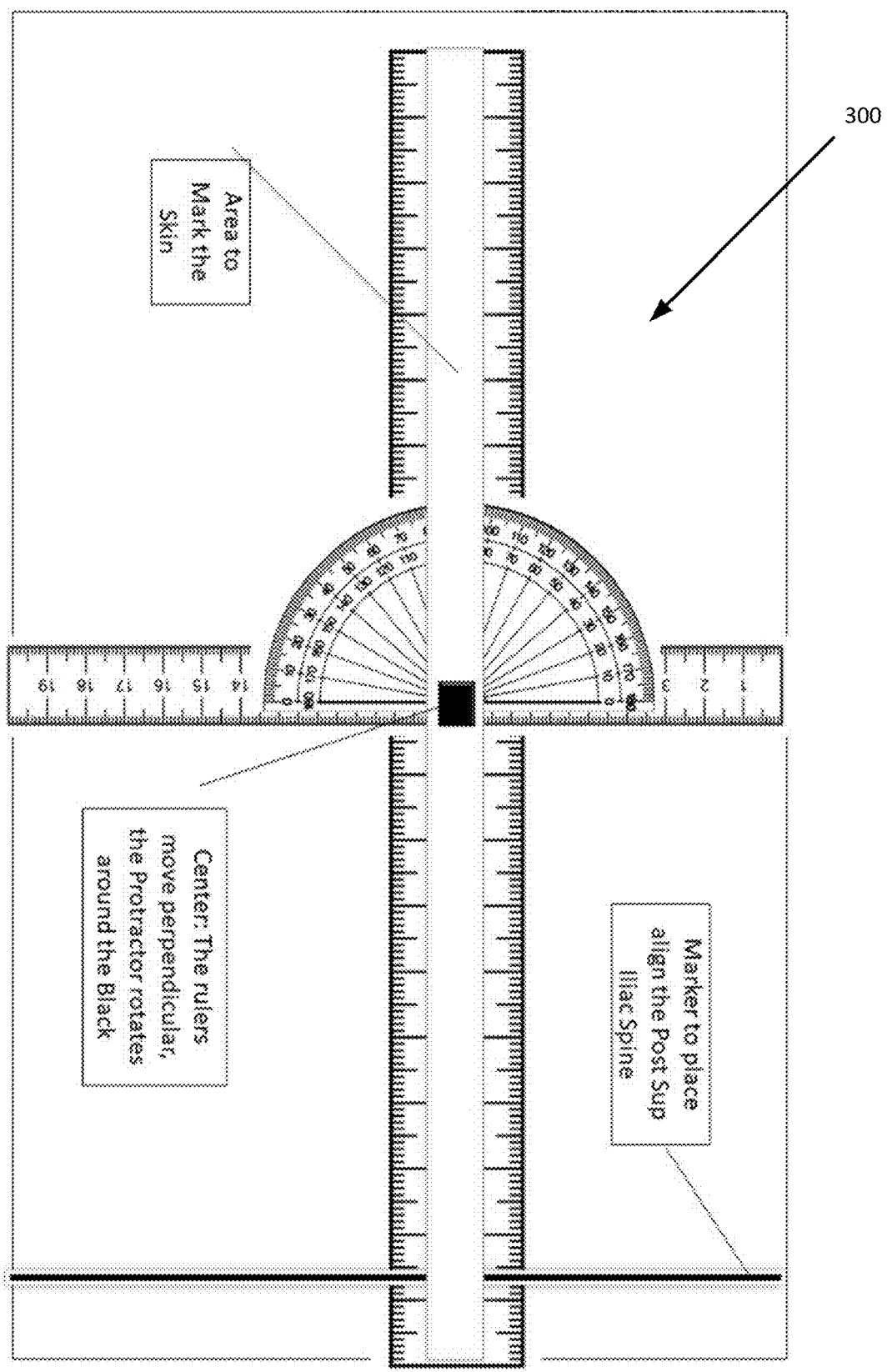
FIG. 5 is a detailed top view of the angle of insertion device of FIG. 3.
Figure 6:
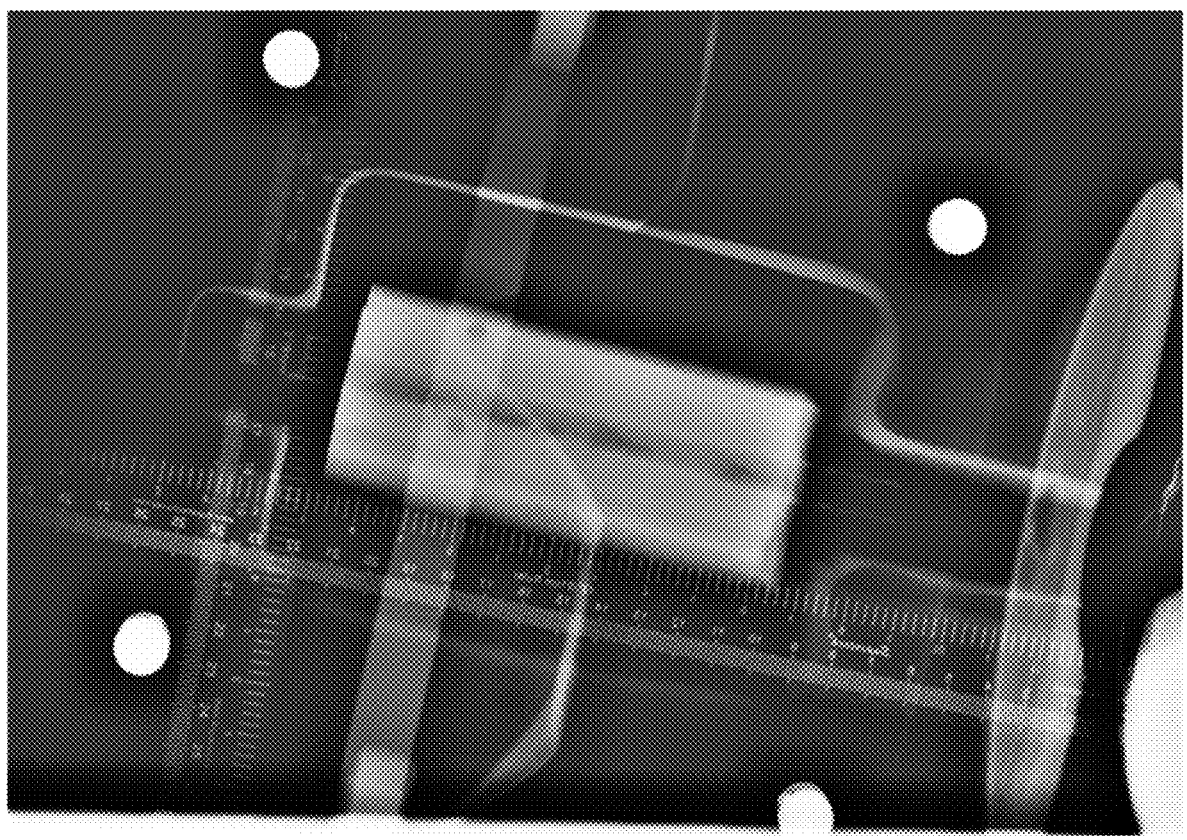
FIG. 6 shows a test X-ray of a lumbar puncture being performed on a manikin using the device for locating a position in a body of FIG. 1.
Figure 7:
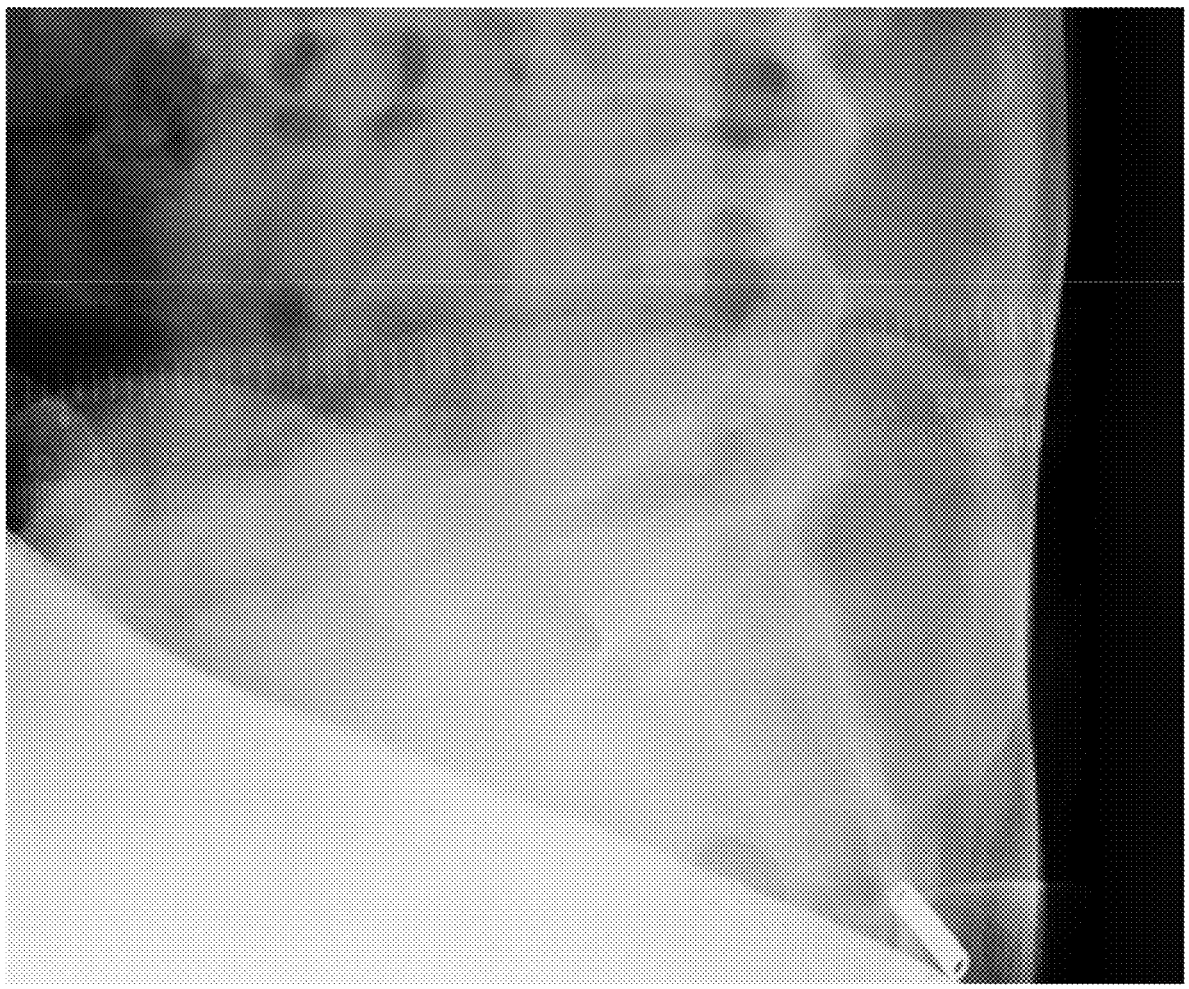
FIG. 7 shows a test X-ray of a lumbar puncture being performed on a person using the angle of insertion device of FIG. 3.
Figure 8:
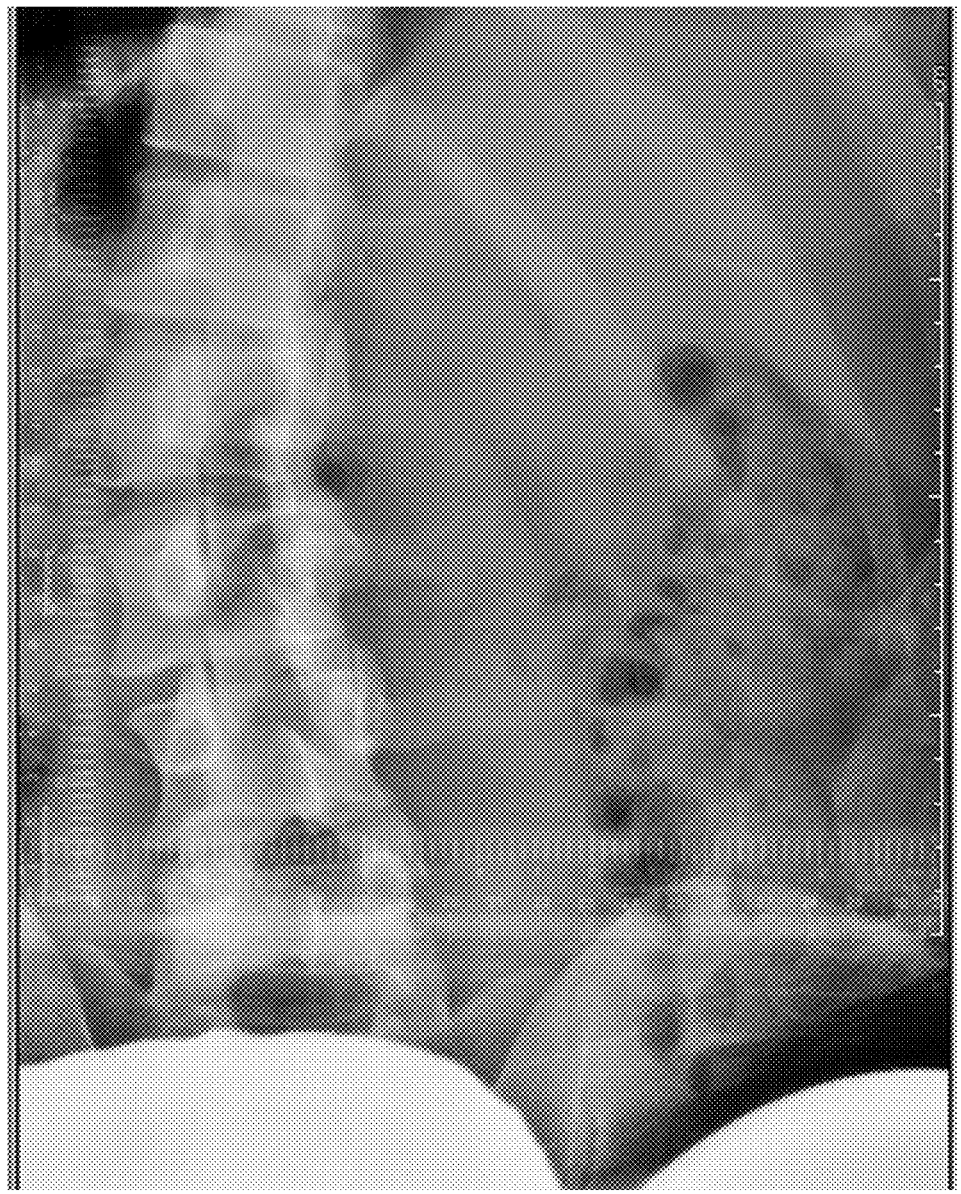
FIG. 8 shows a test X-ray of the device for locating a position in a body of FIG. 1. on a person.
Figure 9:
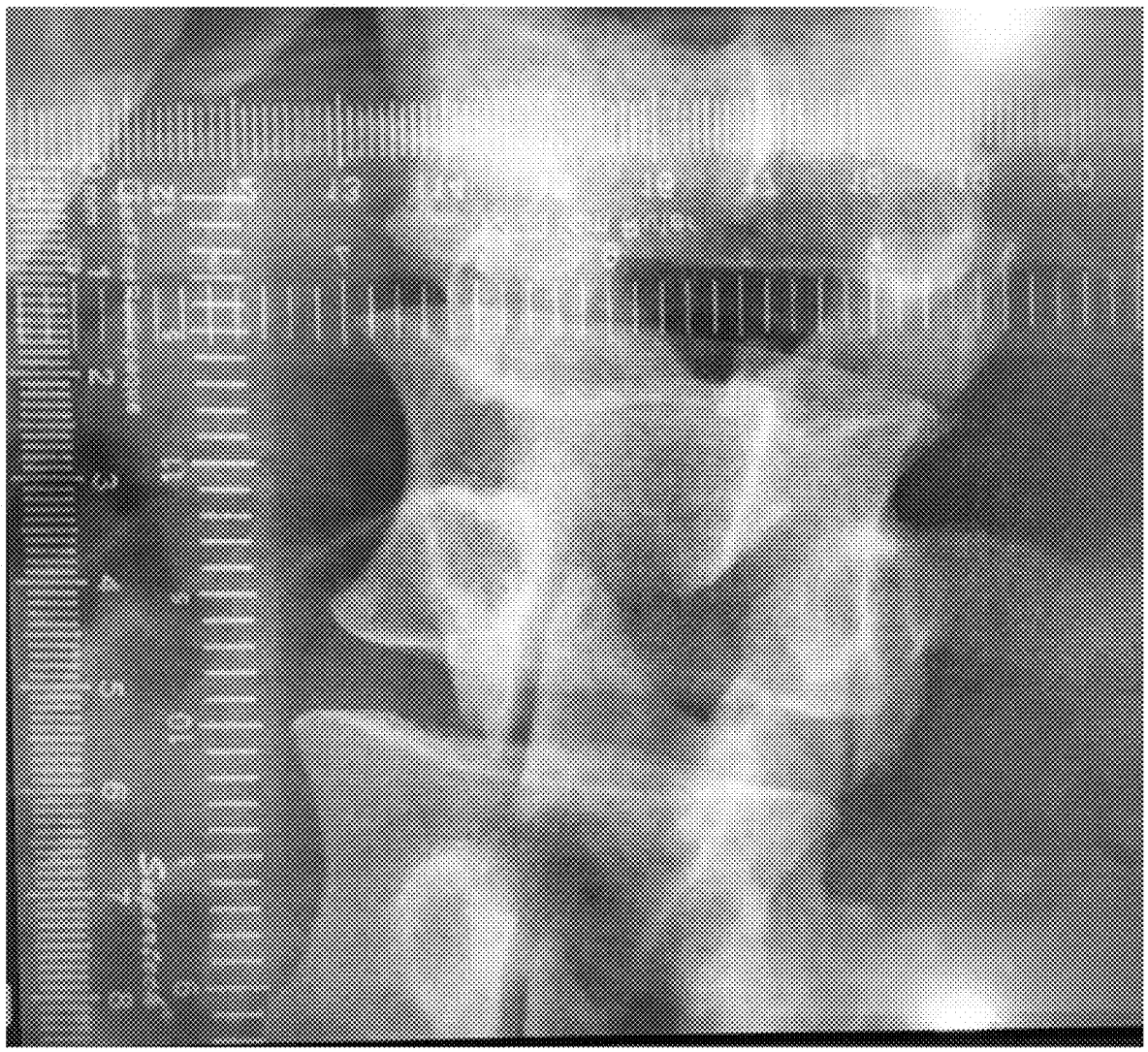
FIG. 9 shows a detail view of a test X-ray of a location of an area to perform a lumbar puncture on a patient located by the device for locating a position in a body of FIG. 1.
Figure 10:
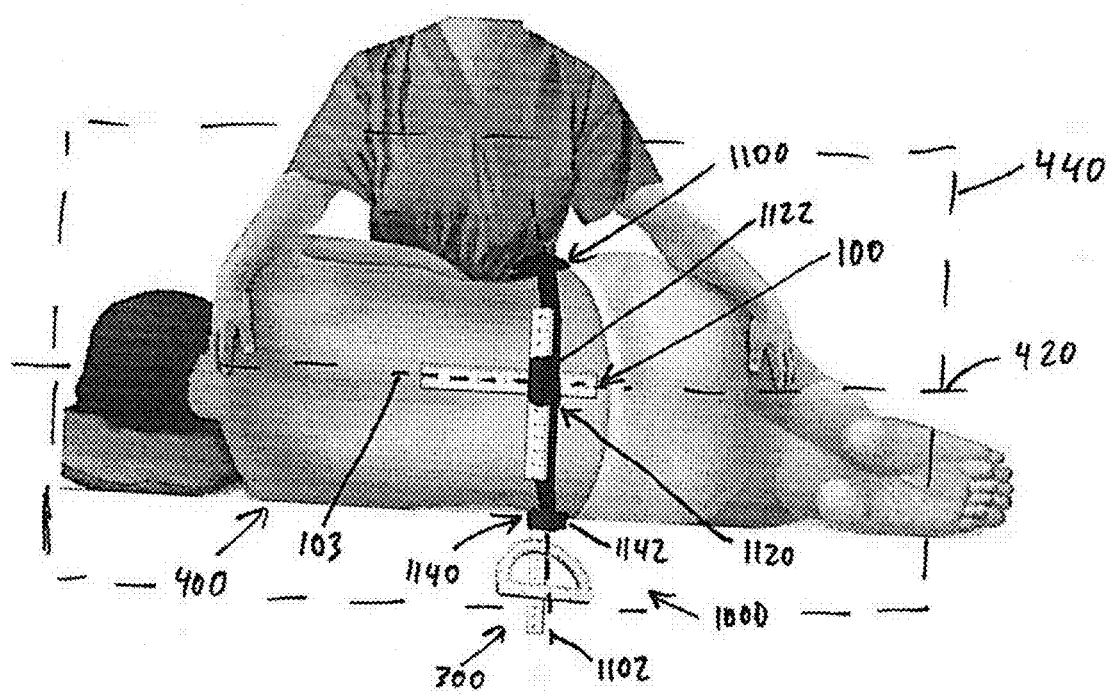
FIG. 10 shows a perspective view of a system for locating a position in a body with a belt disposed around the body of a patient, according to one implementation.
Figure 11:
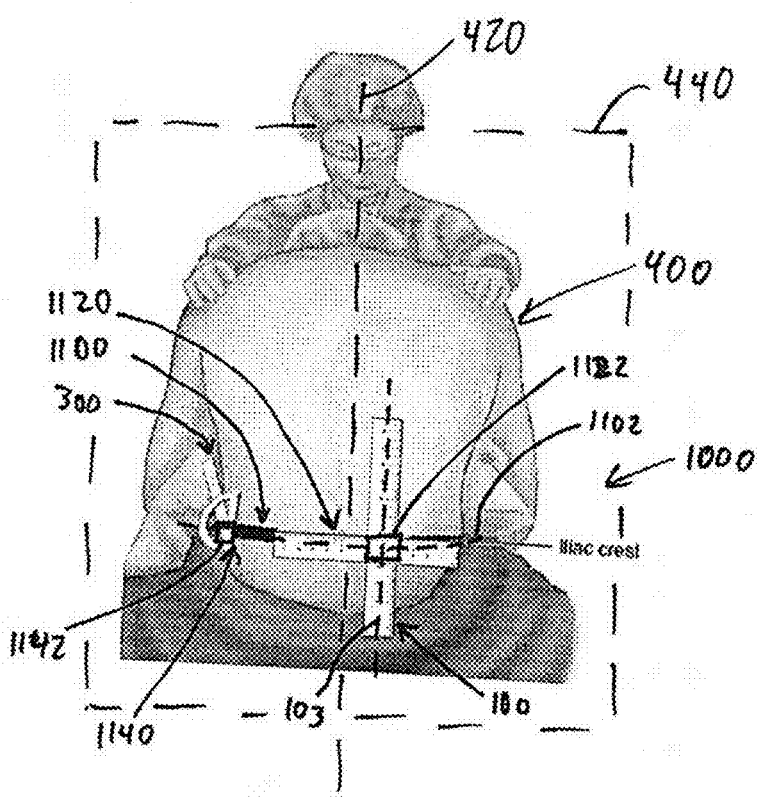
FIG. 11 shows a perspective view of the system for locating a position in a body of FIG. 10 with the belt disposed around the body of a patient.
Figure 12:
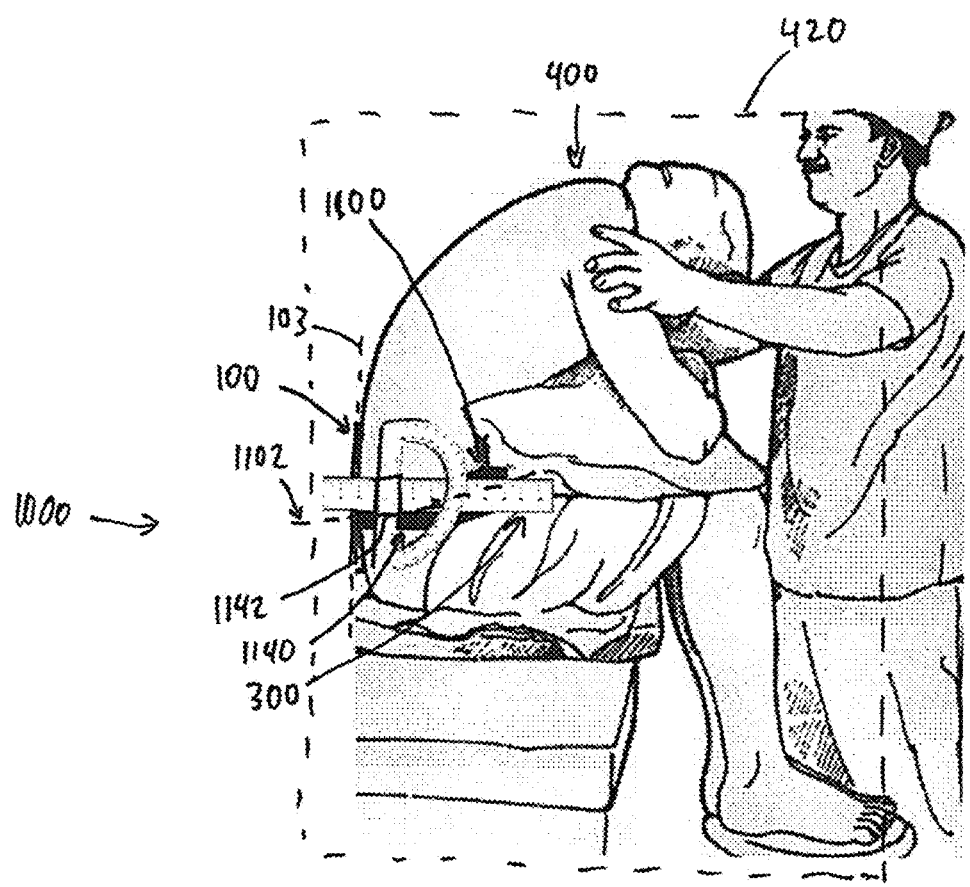
FIG. 12 shows a side view of the system for locating a position in a body of FIG. 10 with the belt disposed around the body of a patient.
Figure 13:
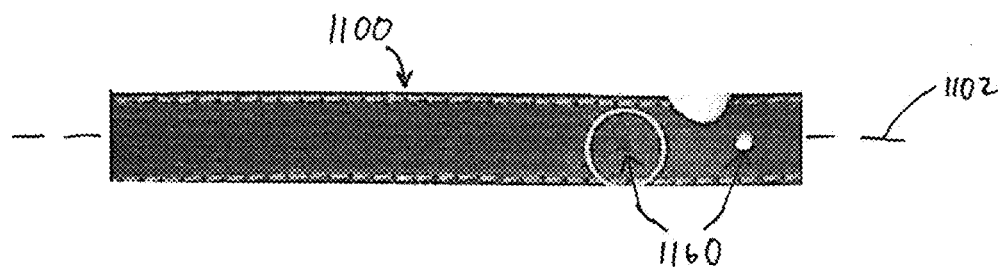
FIG. 13 shows a detail view of the calibration holes of the belt of the system for locating a position in a body of FIG. 10.
Figure 14:
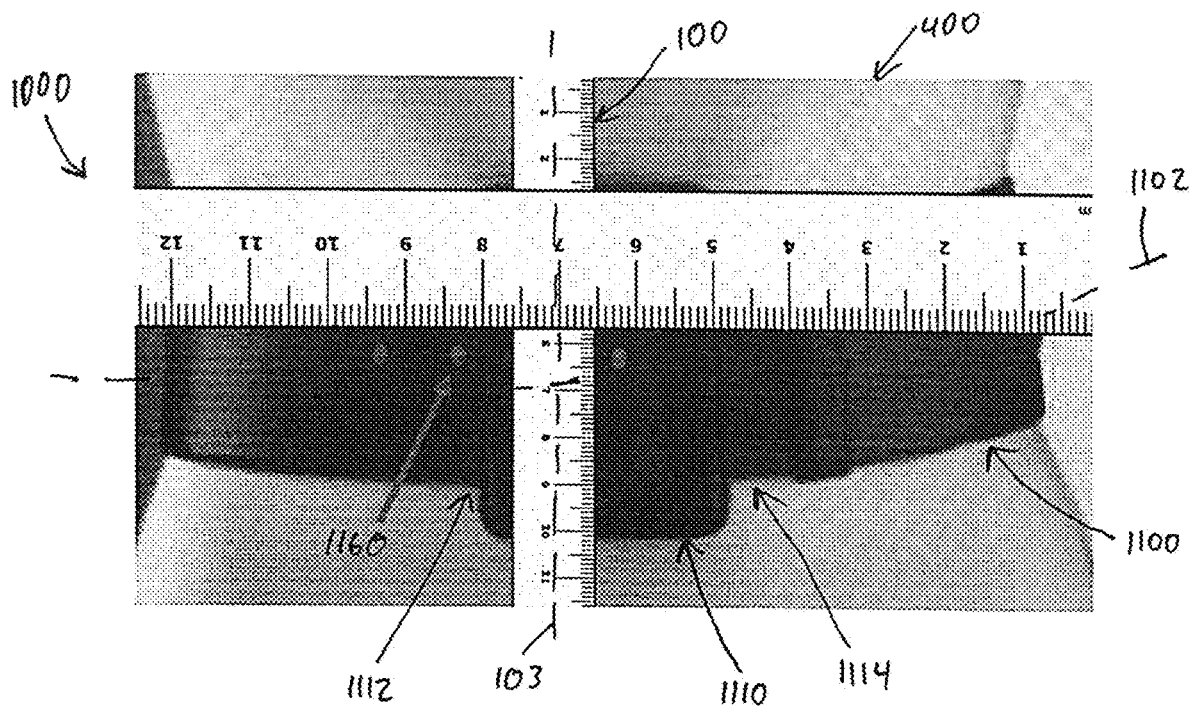
FIG. 14 shows a perspective view of the calibration holes of the belt of the system for locating a position in a body of FIG. 10 with the belt disposed around the body of a patient.

FIGS. 4A, 4B, and 4C show the angle of insertion device 300 in use. FIG. 4A shows an angle of insertion device 300 aligned along a patient's back 404 such that the contact surface 302aa is in physical contact with a patient's back. This arrangement can be implemented when a patient is lying in a lateral decubitis position or when the patient is sitting up, for example. The adhesive 302bb, disposed on the contact surface 302aa, can be used to secure the angle of insertion device 300 to the patient's back in a set position. A user, such as a physician, can place the angle of insertion device 300 against the side of the patient, and produce an image of the angle of insertion device 300 and the patient's body using an X-ray imaging device. The X-ray imaging device can capture the spinal structure of the patient and the radiopaque sets of markers 302b, 304b, 306b. The user can use this X-ray image to determine the position of an intervertebral gap of the patient by using the set of markers 302b, 304b, 306b as X and Y coordinates.

FIGS. 4B and 4C show an angle of insertion device 300 aligned with the curvature of a spinal column 402. The angle of insertion device 300 is aligned perpendicular to the sagittal plane of the subject with the first body portion aligned with the position of the intervertebral gap determined in the first X-ray image. With the angle of insertion device 300 against the side of the patient, a second X-ray image of the angle of insertion device 300 and the patient's body can be produced. The X-ray imaging device captures the spinal structure of the patient and the radiopaque surface of the angle of insertion device 300 markers 302b, 304b, 306d. The user can then determine a depth of the intervertebral gap relative to the patient's back using the set of markers 302b of the first body portion 302 and an angle of the intervertebral gap (angle of insertion) using the set of markers 306d.

These aspects can be measured and marked on the patient's body to determine the proper insertion point, depth, and angle for a lumbar puncture. As such, a user can determine a position and an angle of insertion for an instrument into the intervertebral space based on two X-ray images using the angle of insertion device 300.

FIGS. 10-14 show an implementation of a system 1000 for locating a position in a body. The system includes the device for locating a position in a body 100 and the angle of insertion device 300 described above, and also includes a belt 1100.

The belt 1100 includes a buckle 1110 coupling one end of the belt 1112 to a portion of the belt 1114 to form a loop for disposing around the body of a patient 400. The portion of the belt 1114 to which the buckle 1110 is coupled is selectable based on the circumference of the body of the patient 400.

When the buckle 1110 of the belt 1100 is coupled to a portion of the belt 1114 to form a loop, the belt 1100 has a dorsal belt portion 1120 and a side belt portion 1140. The dorsal belt portion 1120 is disposed adjacent a sagittal plane 420 on the dorsal side of a patient 400 near the spine of the patient 400 when wearing the belt 1100. The side belt portion 1140 is disposed adjacent a coronal plane 440 of the patient 400 when wearing the belt 1100.

The dorsal belt portion 1120 includes a first coupler 1122 for slidably coupling the device for locating a position in a body 100 to the belt 1100. When coupled to the belt 1100, the device for locating a position in a body 100 is positioned such that the first longitudinal axis 103 of the device for locating a position in a body 100 is parallel to the sagittal plane 420 of a patient 400 wearing the belt 1100 and adjacent the spine of the patient 400. The first coupler 1122 is slidable along a belt longitudinal axis 1102 such that the device for locating a position in a body 100 can be moved to a desired position relative to the patient 400. Once the device for locating a position in a body 100 is in the desired position relative to the patient 400, the first coupler 1122 can be locked into a position relative to the belt 1100 such that the device for locating a position in a body 100 can no longer slide relative to the belt 1100 along the belt longitudinal axis 1102.

The device for locating a position in a body 100 is also slidable along the first longitudinal axis 103 such that the device for locating a position in a body 100 can be moved relative to the belt 1100 along the first longitudinal axis 103 to place the device for locating a position in a body 100 in the desired position. Once the device for locating a position in a body 100 is in the desired position relative to the patient 400, the device for locating a position in a body 100 can be locked into a position relative to the belt 1100 such that the device for locating a position in a body 100 can no longer slide relative to the belt 1100 along the first longitudinal axis 103 of the device for locating a position in a body 100.

Although the first coupler 1122 shown in FIGS. 10-14 is slidable along the belt longitudinal axis 1102, in other implementations, the first coupler is fixedly coupled to the dorsal belt portion and the belt must be repositioned on the patient to adjust the position of the device for locating a position in a body relative to the patient. Although the device for locating a position in a body 100 shown in FIGS. 10-14 is slidably coupled to the dorsal belt portion 1120, in other implementations, the device for locating a position in a body is fixedly coupled to the dorsal belt portion and the belt must be repositioned on the patient to adjust the position of the device for locating a position in a body relative to the patient.

The side belt portion 1140 includes a second coupler 1142 for slidably coupling the angle of insertion device 300 to the belt. The second coupler 1142 is slidable along the belt longitudinal axis 1102 such that the angle of insertion device 300 can be moved to a desired position relative to the patient 400. Once the angle of insertion device 300 is in the desired position relative to the patient 400, the second coupler 1142 can be locked into a position relative to the belt 1100 such that the angle of insertion device 300 can no longer slide relative to the belt 1100 along the belt longitudinal axis 1102.

The angle of insertion device 300 is also slidable parallel to the first longitudinal axis 103 of the device for locating a position in a body 100 such that the angle of insertion device 300 can be moved relative to the belt 1100 parallel to the first longitudinal axis 103 to place the angle of insertion device 300 in the desired position. Once the angle of insertion device 300 is in the desired position relative to the patient 400, the angle of insertion device 300 can be locked into a position relative to the belt 1100 such that the angle of insertion device 300 can no longer slide relative to the belt 1100 parallel to the first longitudinal axis 103 of the device for locating a position in a body 100.

Although the second coupler 1142 shown in FIGS. 10-14 is slidable along the belt longitudinal axis 1102, in other implementations, the second coupler is fixedly coupled to the side belt portion and the belt must be repositioned on the patient to adjust the position of the angle of insertion device relative to the patient. Although the angle of insertion device 300 shown in FIGS. 10-14 is slidably coupled to the side belt portion 1140, in other implementations, the angle of insertion device is fixedly coupled to the side belt portion and the belt must be repositioned on the patient to adjust the position of the angle of insertion device relative to the patient.

The belt 1100 defines two calibration holes 1160 extending from an outer surface 1104 of the belt 1100 to an inner surface 1106 of the belt 1100. Once the belt 1100 has been disposed around the body of the patient 400, the skin of a patient 400 wearing the belt 1100 can be marked through each of the calibration holes 1160. Throughout a procedure, the calibration holes 1160 can be monitored to ensure that the marks on the skin of the patient 400 are still visible through both of the calibration holes 1160. If the marks on the skin of the patient 400 are not visible through both of the calibration holes 1160, then this indicates that the position of the belt 1100 has moved relative to the body of the patient 400 and that the measurements made with the system 1000 must be taken again.

The belt 1100 defines at least two calibration holes 1160 to accurately indicate that the belt 1100 has not moved relative to the body of the patient 400 during a procedure. During a procedure, a belt 1100 defining only a single calibration hole 1160 could move such that the plane defined by the longitudinal axis 1102 of the belt 1100 pivots at the single calibration hole 1160. In this scenario, the mark on the skin of the patient 400 would still be visible through the single calibration hole 1160 even though the position of the rest of the belt 1100 had moved relative to the body of the patient 400. By including at least two calibration holes 1160 in the belt 1100, a pivot of the position of the belt 1100 at one calibration hole 1160 would result in the marks on the skin of the patient 400 not being visible through the other calibration holes 1160, indicating that the position of the belt 1100 has changed. Although the belt 1100 shown in FIGS. 10-14 defines two calibration holes 1160, in other implementations, the belt can define one or more than two calibration holes. Although the belt 1100 included in system 1000 defines calibration holes 1160, in other implementations, the device for locating a position in a body 100, the angle of insertion device 300, or both include calibration holes 1160.

EXAMPLE IMPLEMENTATION

FIGS. 5-9 illustrate the example implementations described below. The present implementation is a method and device for performing a bedside lumbar puncture (LP) using a partially radiopaque device and portable X-ray. This method is intended for use in difficult cases due to body habitus, spinal curves including moderate to severe scoliosis, or after failed initial bedside attempt using body landmarks or ultrasound. Also, this method and device is intended to be used in intubated cases with difficulty performing LP at the bedside for patients with deformed spinal anatomy due to trauma or prior spinal surgeries, or in sensitive cases in which a limited number of lumbar puncture attempts are possible, such as with patients taking blood thinners. The device is reusable, and a clear cover is used for each patient. Depending on the position to do the LP, or based on the need of opening pressure or being intubated, the LP would be done in lateral decubitus or sitting up. When the LP is done in a lateral decubitus position, the patient is laying on one side, with hips and knees flexed at 90 degrees and chin flexed toward the chest (fetal position). To maintain horizontal spine positioning, the patient's shoulders and hips can each be aligned vertically. The device can be covered in a one-time use plastic such as an ultrasound probe cover. The patient's iliac crests are palpated, and the device is adhered to the back with the longitudinal axis of the first body portion of the device placed between the crests.

The device has two lead-free, radio-translucent rulers with radiopaque markers which can be moved individually, but perpendicularly during use. A user, such as a physician, can place the dotted line (longitudinal axis) along the spinal process (middle of spine) and the ruler 1 cm far from the dotted line (spine center). This distance is to ensure that the ruler markers will not be obscured by vertebrae or spinous processes when an X-ray is taken. A lead apron over the hip area (up to the posterior superior iliac spine ("PSIS")) and neck belt can protect the other areas of the body from exposure.

The device can be used on a patient in the lateral decubitus position. Once properly positioned, the device is secured to the patient's back using adhesive tape. The longitudinal axis of the first body portion of the device can be aligned with the iliac crest. The first body portion positioning will localize the intervertebral space including the most common targets of L3-L4 and L4-L5 intervertebral space. The second body portion positioning will localize the possible width in which the LP can be done. After the device is adhered securely, the X-ray cassette is placed posterior to the patient (with no gap between the cassette and the device), parallel to the patient's back, with the cassette ideally centered around L4. The board is secured using the bed safety rail and an AP X-ray is performed. The measurements of the first body portion and the second body portion obtained from the AP X-ray provides the ideal measured location of needle insertion on the patient's back—both distance from the PSIS and width of intervertebral space. These measurements can be marked with a pen and the device can be removed. The sterile setting can then be started to perform the LP. If due to obesity of the patient or safety reasons the depth or angle of the needle insertion is also desired, a second X-ray can be taken.

While the patient is in the lateral decubitus position, the device is placed under the patient and the cassette is placed below the device. The longitudinal axis of the first body portion is aligned with the PSIS, and the first body portion is positioned over the dotted line and along the patient's spine, making sure the patient is completely laying over the ruler, with the start point (longitudinal axis of the first body portion of the device) aligned with the iliac crest. The first body portion positioning will localize the L3-L4 and L4-L5 intervertebral space and the second body portion of the device will define the depth from the back of the patient to the targeted intervertebral space.

It is important that X-ray cassettes are removed carefully, and with the least movement, removed from underneath the patient while the provider holds the patient's hip and neck to maintain positioning and degree of spinal flexion.

The device can also be used while the patient is sitting in the upright position rather than lateral decubitus. After the device is adhered to the back using instructions like lateral decubitus, the cassette will be placed behind the device and secured using the bedside rail. If the depth is also needed, another X-ray imaging is needed. The device is adhered to the side of the patient, and the cassette is placed behind it. After the X-ray is taken, the imaging is sent to the electronic medical record (EMR). Based on the measurements, the exact location for lumbar puncture will be marked and the device will be removed from the back. The patient continues to stay in the lateral decubitus or sitting up position with help from the nursing staff. The area will be cleansed and draped in usual sterile fashion, making sure that the markings are not completely removed by cleansing). The rest of the LP procedure, including anesthesia using lidocaine, is like any other routine LP procedure. For a typical adult, a 20-gauge 3.5-inch spinal needle will be placed in the L4-L5 interspace. However, for obese patients, a longer and thicker spinal needle can be used.

As an alternative to bedside lumbar puncture, the performing physician can attempt LPs using ultrasound guidance (if comfortable and familiar with ultrasound) or consult radiology for a fluoroscopy-guided LP. While physicians in internal medicine, emergency medicine, and neurology have historically performed lumbar punctures, radiologists are now the dominant provider of this procedure. Many clinical facilities, particularly small hospitals or clinics in rural or underserved communities, are not equipped with radiologists on-site to perform this procedure. However, access to X-ray is common. Therefore, in an emergency or ambulatory setting, when CSF analysis is desired, the devices and methods disclosed herein provide a way for providers to utilize available technology to perform the procedure successfully.

Lifetime exposure to ionizing radiation is a concern to patients and providers. However, as radiologists increasingly perform fluoroscopy-guided lumbar punctures (FGLP), patients are exposed to increasing levels of radiation. One way to quantify the radiation exposure is the mean dose area product, or DAP, which is the absorbed dose of radiation multiplied by the area irradiated. The average DAP of a FGLP procedure is related to the duration of the procedure and whether the radiologist uses continuous or pulsed fluoroscopy. For FGLP, the DAP can be 10-20 times greater than an AP (anterior-posterior) lumbar spine X-ray. Rather than using continuous fluoroscopy, the devices and methods disclosed herein utilize two X-ray images to achieve a similar result with less exposure to ionizing radiation.

When bedside LP attempts are unsuccessful and FGLP is pursued, it results in an increased cost to the patient. Through the use of X-ray, the devices and methods disclosed herein provide the patient with prompt medical care due to wide availability to X-ray, lower doses of ionizing radiation, and fewer costs. Example practical and commercial applications of the devices and methods disclosed herein can include, but are not limited to, the following examples: (1) if the LP has failed at the bedside using landmarks or ultrasound techniques, (2) if there is a need of urgent LP and there is no availability of interventional radiology, (3) to decrease the need of interventional radiology procedures and decrease the need of hospitalization time, (4) in patients on anticoagulation or other situations which attempts are limited, and (5) to decrease the number of attempts/increase the chance of success of the LP, especially in patients with phobia to the lumber puncture.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

The invention claimed is:

1. A device for locating a position in a body, the device comprising:
   a first body portion having a first longitudinal axis;
   a second body portion slidably coupled to the first body portion, the second body portion having a second longitudinal axis;
   a first set of markers disposed on the first body portion for measuring along the first longitudinal axis, the first set of markers comprising at least two radiopaque markers; and
   a second set of markers disposed on the second body portion for measuring along the second longitudinal axis, the second set of markers comprising at least two radiopaque markers,
   wherein:
      the first body portion is slidable along the second longitudinal axis, and
      the second body portion is slidable along the first longitudinal axis.

2. The device of claim 1, wherein the first longitudinal axis is disposed perpendicular to the second longitudinal axis.

3. The device of claim 1, wherein the first set of markers measure distance along the first longitudinal axis.

4. The device of claim 1, wherein the second set of markers measure distance along the second longitudinal axis.

5. The device of claim 1, wherein the first body portion and the second body portion are radio-translucent.

6. The device of claim 1, further comprising an adhesive material disposed on a surface of the first body portion, the second body portion, or both.

7. The device of claim 1, wherein the first body portion and the second body portion are made of an acrylic material.

8. The device of claim 1, further comprising:
   a protractor body portion coupled to the first body portion and the second body portion; and
   a set of protractor markers disposed on the protractor body portion for measuring an angle relative to the first longitudinal axis, the set of protractor markers comprising at least two radiopaque markers.

9. The device of claim 8, wherein the protractor body portion is slidable along the first longitudinal axis.

10. The device of claim 8, wherein the protractor body portion is radio-translucent.

11. An angle of insertion device, the device comprising:
a first body portion having a longitudinal axis;
a protractor body portion coupled to the first body portion;
a first set of markers disposed on the first body portion for measuring along the longitudinal axis, the first set of markers comprising at least two radiopaque markers; and
a set of protractor markers disposed on the protractor body portion for measuring an angle relative to the longitudinal axis, the set of protractor markers comprising at least two radiopaque markers.

12. The device of claim 11, wherein the protractor body portion is slidable along the first longitudinal axis.

13. The device of claim 11, wherein the first set of markers measure distance along the first longitudinal axis.

14. The device of claim 11, wherein the first body portion and the protractor body portion are radio-translucent.

15. The device of claim 11, further comprising an adhesive material disposed on a surface of the first body portion, the protractor body portion, or both.

16. The device of claim 11, wherein the first body portion and the protractor body portion are made of an acrylic material.

17. The device of claim 11, wherein the longitudinal axis is a first longitudinal axis, the device further comprising:
a second body portion slidably coupled to the first body portion, the second body portion having a second longitudinal axis; and
a second set of markers disposed on the second body portion for measuring along the second longitudinal axis, the second set of markers comprising at least two radiopaque markers.

18. The device of claim 17, wherein:
the first body portion is slidable along the second longitudinal axis, and
the second body portion is slidable along the first longitudinal axis.

19. A system for locating a position in a body, the system comprising:
a first device for locating a position in a body, the first device comprising:
a first body portion of the first device having a first longitudinal axis,
a second body portion of the first device slidably coupled to the first body portion of the first device, the second body portion of the first device having a second longitudinal axis,
a first set of markers of the first device disposed on the first body portion of the first device for measuring along the first longitudinal axis, the first set of markers of the first device comprising at least two radiopaque markers of the first device, and
a second set of markers of the first device disposed on the second body portion of the first device for measuring along the second longitudinal axis, the second set of markers of the first device comprising at least two radiopaque markers of the first device, wherein:
the first body portion of the first device is slidable along the second longitudinal axis, and
the second body portion of the first device is slidable along the first longitudinal axis;
a second device for determining an angle of insertion, the second device comprising:
a first body portion of the second device having a longitudinal axis;
a protractor body portion coupled to the first body portion of the second device;
a first set of markers of the second device disposed on the first body portion of the second device for measuring along the longitudinal axis, the first set of markers of the second device comprising at least two radiopaque markers of the second device; and
a set of protractor markers disposed on the protractor body portion for measuring an angle relative to the longitudinal axis, the set of protractor markers comprising at least two radiopaque markers; and
a belt for being disposed around a waist and/or hips of a person, the belt comprising:
a dorsal belt portion for being disposed adjacent a sagittal plane on a dorsal side of the person, the dorsal belt portion including a first coupler for coupling the first device for locating a position in a body to the belt,
a side belt portion for being disposed adjacent a coronal plane of the person, the side belt portion including a second coupler for coupling the second device for determining an angle of insertion device to the belt.

20. The system of claim 19, wherein the first coupler and second coupler are slidable relative to the belt along a belt longitudinal axis, and wherein the first device for locating a position in a body is slidably couplable to the first coupler and the second device for determining the angle of insertion is slidably couplable to the second coupler of the side belt portion.

* * * * *